(12) United States Patent
Arai

(10) Patent No.: US 11,973,639 B2
(45) Date of Patent: Apr. 30, 2024

(54) INFORMATION PROCESSING SYSTEM, INFORMATION PROCESSING METHOD, AND RECORDING MEDIUM

(71) Applicant: Shohei Arai, Kanagawa (JP)

(72) Inventor: Shohei Arai, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 18/067,280

(22) Filed: Dec. 16, 2022

(65) Prior Publication Data

US 2023/0208706 A1 Jun. 29, 2023

(30) Foreign Application Priority Data

Dec. 27, 2021 (JP) .................................. 2021-212728
Dec. 1, 2022 (JP) .................................. 2022-193098

(51) Int. Cl.
*H04L 41/0681* (2022.01)
*A61B 5/00* (2006.01)

(52) U.S. Cl.
CPC ........ *H04L 41/0681* (2013.01); *A61B 5/0022* (2013.01)

(58) Field of Classification Search
CPC .............. H04L 41/0686; H04L 41/0681; H04L 41/069; A61B 5/0022; A61B 5/0024
See application file for complete search history.

(56) References Cited

U.S. PATENT DOCUMENTS

| | | | | |
|---|---|---|---|---|
| 9,767,677 B1 * | 9/2017 | Paulin | .................. | G08B 25/005 |
| 10,729,371 B2 * | 8/2020 | Abreu | ................ | A61B 5/02416 |
| 10,786,693 B1 * | 9/2020 | Opperman | ............. | A62B 18/02 |
| 11,094,337 B2 * | 8/2021 | Daimo | .................... | G10L 25/51 |
| 11,123,021 B2 * | 9/2021 | Shikii | .................... | A61B 5/165 |
| 11,456,080 B1 * | 9/2022 | Jain | ...................... | A61B 5/4815 |
| 11,504,011 B1 * | 11/2022 | Jain | .......................... | G06N 5/04 |
| 11,514,738 B2 * | 11/2022 | Luthra | ................... | G16H 40/67 |
| 11,783,652 B2 * | 10/2023 | Chaurasia | ............. | G16H 40/63 340/5.2 |
| 11,838,365 B1 * | 12/2023 | Jain | ........................ | G16H 20/10 |

(Continued)

FOREIGN PATENT DOCUMENTS

| | | |
|---|---|---|
| JP | 2006-333114 | 12/2006 |
| JP | 2021-064063 | 4/2021 |

*Primary Examiner* — Sargon N Nano

(74) *Attorney, Agent, or Firm* — IPUSA, PLLC

(57) ABSTRACT

A system, a method, and a program stored on a recording medium are provided each of which receives a first setting and a second setting input to a terminal apparatus, the first setting indicating a transmission destination of a notification based on information related to health of a user obtained through measurement by a measurement apparatus managed by a health check system, the second setting indicating a notification condition on which the notification is transmitted to the transmission destination; receives the information related to health of the user obtained through measurement by the measurement apparatus and transmitted from the measurement apparatus to the health check system; and transmits the notification based on the information related to health of the user to the transmission destination indicated by the first setting, in response to the information related to health of the user satisfying the notification condition indicated by the second setting.

9 Claims, 14 Drawing Sheets

| FIELD | DATA FORMAT | EXPLANATION | EXAMPLE VALUE |
|---|---|---|---|
| id | INT | USER ID REGISTERED IN HEALTH CHECK SYSTEM | userA |
| began_timestamp | DateTime | – | 2021-06-01T07:05:25 |
| end_timestamp | DateTime | – | 2021-06-01T07:05:40 |
| device_id | INT | ID OF KIOSK TERMINAL OF HEALTH CHECK SYSTEM | 3168 |
| session_id | String | ID OF HEALTH DATA | xxx123456 |
| temperature | INT | BODY TEMPERATURE | 95.0 |
| sanitizer | Boolean | WHETHER VISITOR HAS USED HAND SANITIZER | True |
| symptoms | Boolean | WHETHER VISITOR HAS ANY SYMPTOM | False |
| mask_detection | MASK OK, MASK NOT OK, NO MASK, Unknown | STATE OF MASK | MASK_OK |
| : | : | : | : |

(56) References Cited

U.S. PATENT DOCUMENTS

| | | | |
|---|---|---|---|
| 2017/0189637 A1* | 7/2017 | Fateh | A61B 5/443 |
| 2018/0322946 A1* | 11/2018 | Ika | G06F 21/6254 |
| 2019/0009114 A1* | 1/2019 | Han | A41D 1/002 |
| 2020/0076705 A1* | 3/2020 | Kanojia | G06F 3/0484 |
| 2021/0077762 A1* | 3/2021 | Mauger | A61M 16/107 |
| 2021/0107768 A1 | 4/2021 | Nishida | |
| 2021/0304537 A1* | 9/2021 | Reed | G06F 18/22 |
| 2021/0346731 A1* | 11/2021 | Trishaun | A61B 5/6803 |
| 2021/0369212 A1* | 12/2021 | Shikii | A61B 5/7278 |
| 2021/0391089 A1* | 12/2021 | Eswara | G06V 20/53 |
| 2022/0020237 A1* | 1/2022 | Luthra | G07C 9/27 |
| 2022/0036678 A1* | 2/2022 | Parekh | G06V 40/107 |
| 2023/0076864 A1* | 3/2023 | Shoji | G06F 3/16 |

* cited by examiner

| TENANT ID | USER ID | PASSWORD | EMAIL ADDRESS |
|---|---|---|---|
| tenantA | userA | 7xpbct9& | userA@xxx.com |
| tenantA | userA2 | sM#tv0qr | userA2@xxx.com |
| ⋮ | ⋮ | ⋮ | ⋮ |
| tenantB | userB | 6yoads4! | userB@xxx.com |
| ⋮ | ⋮ | ⋮ | ⋮ |

| TENANT ID | TENANT NAME |
|---|---|
| tenantA | TENANT A |
| tenantB | TENANT B |
| ⋮ | ⋮ |

FIG. 8

| SYSTEM ID | TENANT ID | CONNECTION DESTINATION INFORMATION |
|---|---|---|
| SystemA | tenantA | { "host":"xxx.kiosk.com" "apikey":"abcd1234" } |
| ⋮ | ⋮ | ⋮ |

FIG. 9

Notification Rule Setting Screen

- Rule ID: ruleA
- Add
- Delete
- Field: temperature
- Relational operator: >=
- Threshold value: 99.5
- Execute

FIG. 10

| RULE ID | TENANT ID | FIELD | RELATIONAL OPERATOR | THRESHOLD VALUE |
|---------|-----------|-------------|---------------------|-----------------|
| ruleA   | tenantA   | temperature | >=                  | 99.5            |
| ruleB   | tenantB   | temperature | >=                  | 99.0            |
| :       | :         | :           | :                   | :               |

FIG. 11

Notification Transmission Destination Setting Screen

Rule ID: ruleA

Transmission destination: userA2  [Delete]

Transmission destination: userA  [Delete]

[Add]

[Execute]

FIG. 14

| FIELD | DATA FORMAT | EXPLANATION | EXAMPLE VALUE |
|---|---|---|---|
| id | INT | USER ID REGISTERED IN HEALTH CHECK SYSTEM | userA |
| began_timestamp | DateTime | - | 2021-06-01T07:05:25 |
| end_timestamp | DateTime | - | 2021-06-01T07:05:40 |
| device_id | INT | ID OF KIOSK TERMINAL OF HEALTH CHECK SYSTEM | 3168 |
| session_id | String | ID OF HEALTH DATA | xxx123456 |
| temperature | INT | BODY TEMPERATURE | 95.0 |
| sanitizer | Boolean | WHETHER VISITOR HAS USED HAND SANITIZER | True |
| symptoms | Boolean | WHETHER VISITOR HAS ANY SYMPTOM | False |
| mask_detection | MASK OK, MASK NOT OK, NO MASK, Unknown | STATE OF MASK | MASK_OK |
| ⋮ | ⋮ | ⋮ | ⋮ |

FIG. 15

| TENANT ID /73 | DATA GENERATION DATE /74 | HEALTH DATA /75 /72 |
|---|---|---|
| tenantA | MARCH 12, 2021 | { "id":"xxx123456" "began_timestamp":"2021-03-12T09:10:02" ... } |
| ⋮ | ⋮ | ⋮ |

From: no-reply@data-integration.example.com  /131

To: userA@example.com  /132

Subject: Notification about health data  /133

Message body:  /134

A notification about health data from the data integration system

We are informing you that data acquired by the kiosk terminal conforms to the notification rule.

Service name: Kiosk

Data type: Temperature

Data value: 99.8

To stop the delivery of this notification, please click here and change the notification rule.

This email is sent automatically by the system.

XXX Corporation

FIG. 18A

| RULE ID | TENANT ID | DATA TYPE | RELATIONAL OPERATOR | THRESHOLD VALUE |
|---------|-----------|-----------|---------------------|-----------------|
| ruleA | tenantA | dataTypeA | >= | 99.5 |
| : | : | : | : | : |

FIG. 18B

| DATA TYPE | DATA NAME |
|-----------|-----------|
| dataTypeA | temperature |
| : | : |

FIG. 18C

| DATA TYPE | SYSTEM ID | FIELD |
|-----------|-----------|-------|
| dataTypeA | systemA | temperature |
| dataTypeA | systemB | temp |
| : | : | : |

ND RECORDING MEDIUM

INFORMATION PROCESSING SYSTEM, INFORMATION PROCESSING METHOD, AND RECORDING MEDIUM

CROSS-REFERENCE TO RELATED APPLICATIONS

This patent application is based on and claims priority pursuant to 35 U.S.C. § 119(a) to Japanese Patent Application No. 2021-212728, filed on Dec. 27, 2021 and Japanese Patent Application No. 2022-193098, filed on Dec. 1, 2022, in the Japan Patent Office, the entire disclosure of which is hereby incorporated by reference herein.

BACKGROUND

Technical Field

The present disclosure relates to an information processing system, an information processing method, and a recording medium.

Related Art

In some cases, a terminal is provided at the entrance of a building, which acquires health-related data (hereinafter, referred to as "health data") such as a body temperature of an entering person or whether or not the entering person is wearing a mask.

For example, such a terminal transmits the acquired health data to a server. The server transmits a notification to a predetermined transmission destination in response to detecting an abnormality in the health data.

In the related art, however, the transmission destination of the notification based on the health data is fixed. That is, a user is not allowed to freely set the transmission destination.

SUMMARY

Example embodiments include an information processing system communicably connected via a network to a health check system that manages a measurement apparatus and a terminal apparatus. The information processing system includes circuitry. The circuitry receives a first setting and a second setting that are input to the terminal apparatus, from the terminal apparatus via a network. The first setting indicates a transmission destination of a notification based on information related to health of a user obtained through measurement by the measurement apparatus. The second setting indicates a notification condition on which the notification is transmitted to the transmission destination. The circuitry receives, from the health check system via the network, the information related to health of the user obtained through measurement by the measurement apparatus and transmitted from the measurement apparatus to the health check system. The circuitry transmits the notification based on the received information related to health of the user to the transmission destination indicated by the first setting, in response to the received information related to health of the user satisfying the notification condition indicated by the second setting.

Example embodiments include an information processing method including receiving a first setting and a second setting that are input to a terminal apparatus, from the terminal apparatus via a network, the first setting indicating a transmission destination of a notification based on information related to health of a user obtained through measurement by a measurement apparatus managed by a health check system, the second setting indicating a notification condition on which the notification is transmitted to the transmission destination; receiving, from the health check system via the network, the information related to health of the user obtained through measurement by the measurement apparatus and transmitted from the measurement apparatus to the health check system; and transmitting the notification based on the received information related to health of the user to the transmission destination indicated by the first setting, in response to the received information related to health of the user satisfying the notification condition indicated by the second setting.

Example embodiments include a non-transitory recording medium storing a plurality of instructions which, when executed by one or more processors, cause the processors to perform an information processing method including receiving a first setting and a second setting that are input to a terminal apparatus, from the terminal apparatus via a network, the first setting indicating a transmission destination of a notification based on information related to health of a user obtained through measurement by a measurement apparatus managed by a health check system, the second setting indicating a notification condition on which the notification is transmitted to the transmission destination; receiving, from the health check system via the network, the information related to health of the user obtained through measurement by the measurement apparatus and transmitted from the measurement apparatus to the health check system; and transmitting the notification based on the received information related to health of the user to the transmission destination indicated by the first setting, in response to the received information related to health of the user satisfying the notification condition indicated by the second setting.

BRIEF DESCRIPTION OF THE DRAWINGS

A more complete appreciation of embodiments of the present disclosure and many of the attendant advantages and features thereof can be readily obtained and understood from the following detailed description with reference to the accompanying drawings, wherein:

FIG. 8 is a diagram illustrating an example of a connection destination information table according to the embodiment of the present disclosure;

FIG. 9 is a diagram illustrating an example of a notification rule setting screen according to the embodiment of the present disclosure;

FIG. 10 is a diagram illustrating an example of a notification rule table according to the embodiment of the present disclosure;

FIG. 11 is a diagram illustrating an example of a notification transmission destination setting screen according to the embodiment of the present disclosure;

FIG. 14 is a diagram for describing health data according to the embodiment of the present disclosure;

FIG. 15 is a diagram illustrating an example of a health data table according to the embodiment of the present disclosure;

FIG. 16 is a diagram illustrating an example of an email of a notification based on the health data according to the embodiment of the present disclosure;

FIGS. 18A, 18B, and 18C are each a diagram illustrating an example of a notification rule table according to another embodiment of the present disclosure.

Figure 1:
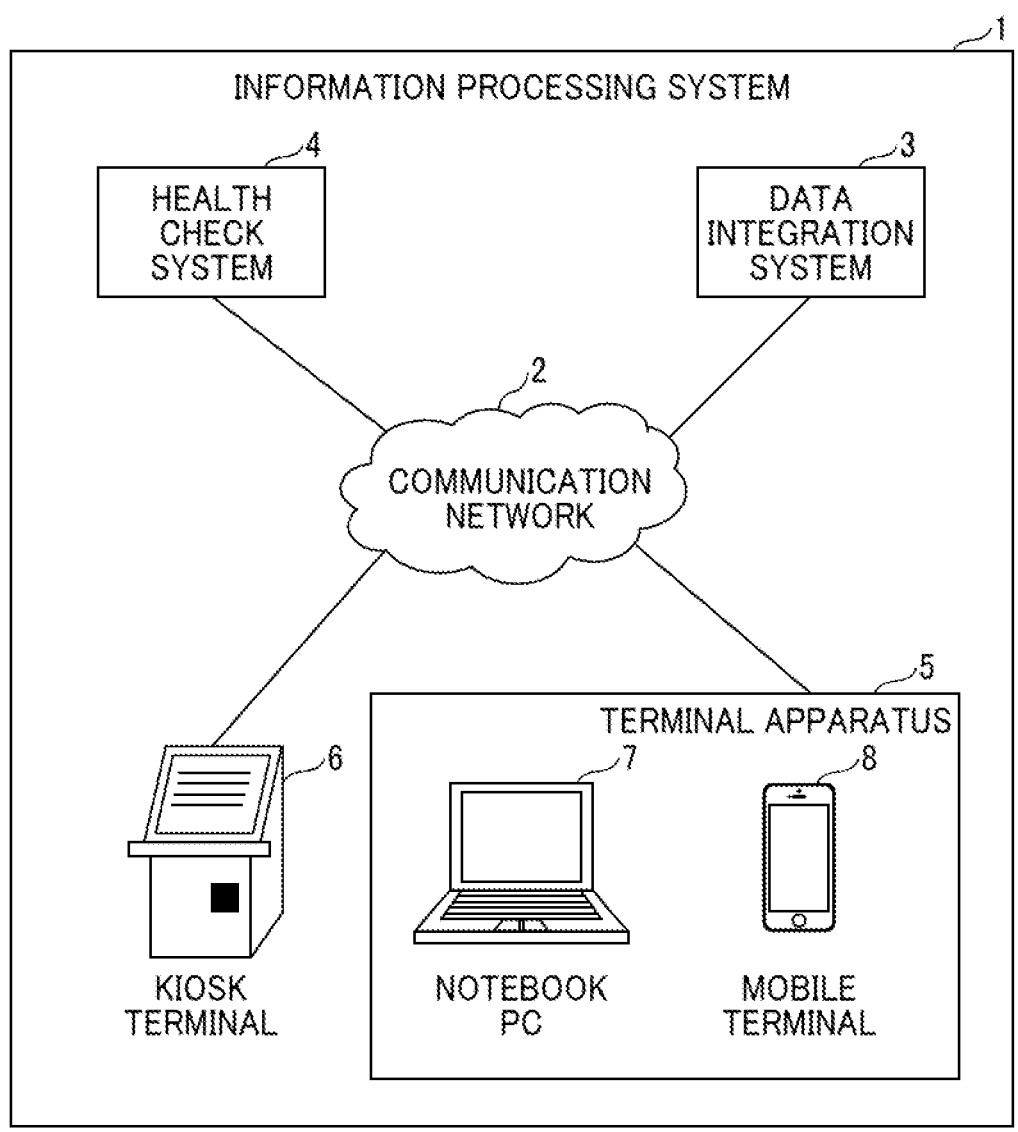
FIG. 1 is a schematic diagram illustrating an example of an information processing system according to an embodiment of the present disclosure.

The accompanying drawings are intended to depict embodiments of the present disclosure and should not be interpreted to limit the scope thereof. The accompanying drawings are not to be considered as drawn to scale unless explicitly noted. Also, identical or similar reference numerals designate identical or similar components throughout the several views.

DETAILED DESCRIPTION

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

Referring now to the drawings, embodiments of the present disclosure are described below. As used herein, the singular forms "a," "an," and "the" are intended to include the plural forms as well, unless the context clearly indicates otherwise.

An information processing system, an information processing apparatus, an information processing method, and a program according to embodiments of the present disclosure will be described in detail below with reference to the accompanying drawings.

First Embodiment

System Configuration

FIG. 1 is a schematic diagram illustrating an example of an information processing system according to a first embodiment of the present disclosure. An information processing system 1 includes, for example, a data integration system 3, a health check system 4, terminal apparatuses 5, and a kiosk terminal 6 that are connected to a communication network 2 such as Internet. The terminal apparatuses 5 are used by users and include a notebook personal computer (PC) 7 and a mobile terminal 8. The kiosk terminal 6 is installed, for example, at an entrance of a building such as an office building and is used for acquiring health data of an entering person such as an employee or visitor who enters the building. The kiosk terminal 6 is an example of a measurement apparatus. The health data is data related to health of an entering person acquired by the data integration system 3. For example, the health data is data used for checking a health condition of an entering person or checking information that affects health of an entering person. Examples of the health condition of an entering person include a body temperature of the entering person. Examples of the information that affect health of an entering person include information as to whether an entering person is wearing a mask and information as to whether an entering person has used hand sanitizer. For example, the kiosk terminal 6 includes a temperature sensor, and the temperature sensor measures a body temperature of an entering person. For example, the kiosk terminal 6 includes a camera. The camera captures an image of an entering person, and recognition is performed on the captured image to detect whether the entering person is wearing a mask. For example, the kiosk terminal 6 includes a sensor. The sensor detects discharge of the hand sanitizer to determine whether an entering person has used the hand sanitizer. The health check system 4 is deployed for each tenant, for example. The kiosk terminal 6 at a certain tenant acquires health data of employees belonging to the tenant or visitors to a building. The kiosk terminal 6 transmits the acquired health data to the health check system 4 belonging to the tenant via the communication network 2. The data integration system 3 is shared among a plurality of tenants. That is, the data integration system 3 provides services (described below) to a plurality of tenants. In the present embodiment, the data integration system 3 that provides services (described below) to a plurality of tenants will be described. However, the data integration system 3 may provide the services to a single tenant.

In this disclosure, the term "tenant" refers to an entity having a contract of utilizing the services provided by the data integration system 3. For example, an organization such as a company or a department in a company is an example of the tenant. That is, the tenant corresponds to a group of users.

If the health data received from the health check system 4 satisfies a condition defined by a notification rule set in advance, the data integration system 3 provides the tenant with a service of transmitting a predetermined notification to a transmission destination set in association with the notification rule. An administrator and a user belonging to the tenant use the notebook PC 7 of the mobile terminal 8 to access the data integration system 3, and set the notification rule and the transmission destination of a notification or check a notification transmitted from the data integration system 3. Identification information (also referred to as an identifier) for identifying and distinguishing an organization such as a tenant is defined for the organization. The notification rule and the transmission destination of a notification are set in association with the identification information.

Note that the configuration of the information processing system 1 illustrated in FIG. 1 is merely an example. For example, the data integration system 3 and the health check system 4 may be cloud systems connectable via the Internet, or may be connected to a company network such as an intra-company local area network (LAN). The terminal apparatuses 5 may reside in a network of a company serving as a tenant, or may be connected to the company network or the communication network 2 from an external network by wired communication or wireless communication such as mobile communication or a wireless LAN.

Example Hardware Configuration

Figure 2:
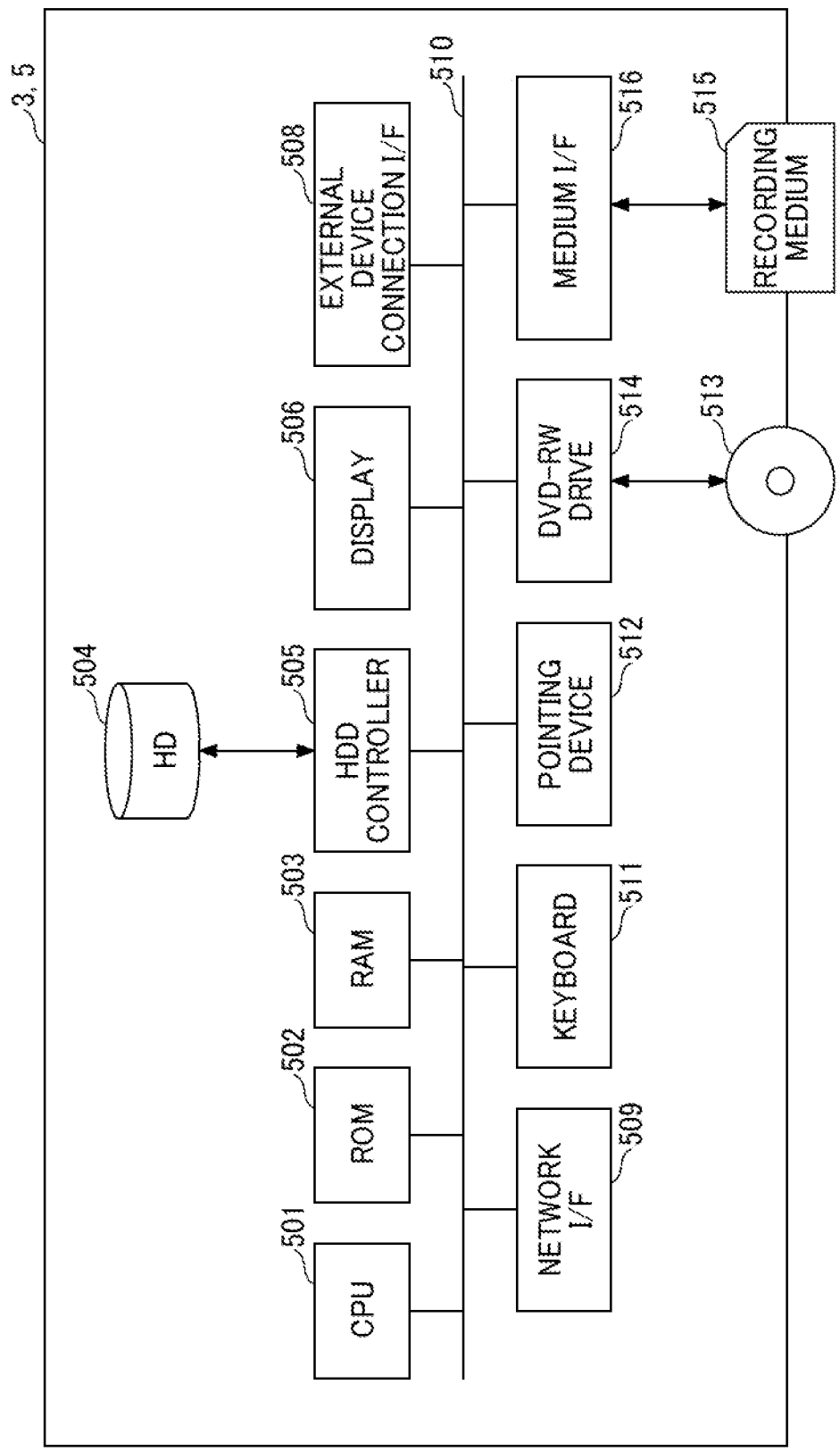
FIG. 2 is a block diagram illustrating an example of a hardware configuration of an information processing apparatus according to the embodiment of the present disclosure.

FIG. 2 is a block diagram illustrating an example of a hardware configuration of an information processing apparatus according to the first embodiment of the present disclosure. The information processing apparatus serves as each of the data integration system 3 and the terminal apparatuses 5 such as the notebook PC 7. As illustrated in FIG. 2, the information processing apparatus is a computer, and includes a central processing unit (CPU) 501, a read-only memory (ROM) 502, a random access memory (RAM) 503, a hard disk (HD) 504, a hard disk drive (HDD) controller 505, a display 506, an external device connection interface (I/F) 508, a network I/F 509, a bus line 510, a keyboard 511, a pointing device 512, a digital versatile disc-rewritable (DVD-RW) drive 514, and a medium I/F 516.

The CPU 501 controls overall operation of the information processing apparatus. The ROM 502 stores programs such as an initial program loader (IPL) to boot the CPU 501. The RAM 503 is used as a work area for the CPU 501. The HD 504 stores various kinds of data such as programs. The HDD controller 505 controls reading or writing of various kinds of data from or to the HD 504 under control of the CPU 501. The display 506 displays various kinds of information such as a cursor, a menu, a window, characters, or an image. The external device connection IF 508 is an interface that connects various external devices to the information processing apparatus. Examples of the external devices include, but are not limited to, a Universal Serial Bus (USB) memory and a printer. The network I/F 509 is an interface that enables communication of data via the communication network 2. The bus line 510 is, for example, an address bus or a data bus, which electrically connects the components such as the CPU 501 illustrated in FIG. 2 to one another.

The keyboard 511 is an example of an input device provided with a plurality of keys with which a user enters characters, numerical values, or various instructions. The pointing device 512 is an example of an input device with which a user selects or executes various instructions, selects a target for processing, or moves a cursor. The DVD-RW drive 514 controls reading or writing of various kinds of data from or to a DVD-RW 513, which is an example of a removable recording medium. The removable recording medium is not limited to the DVD-RW 513 and may be a digital versatile disc-recordable (DVD-R) or the like. The medium I/F 516 controls reading or writing (storing) of data from or to a recording medium 515 such as a flash memory.

The information processing apparatus illustrated in FIG. 2 is merely an example and does not necessarily include all of the components. For example, when the information processing apparatus functions as a server such as the data integration system 3, the keyboard 511 and the pointing device 512 may be omitted from the information processing apparatus.

Functions

Figure 3:
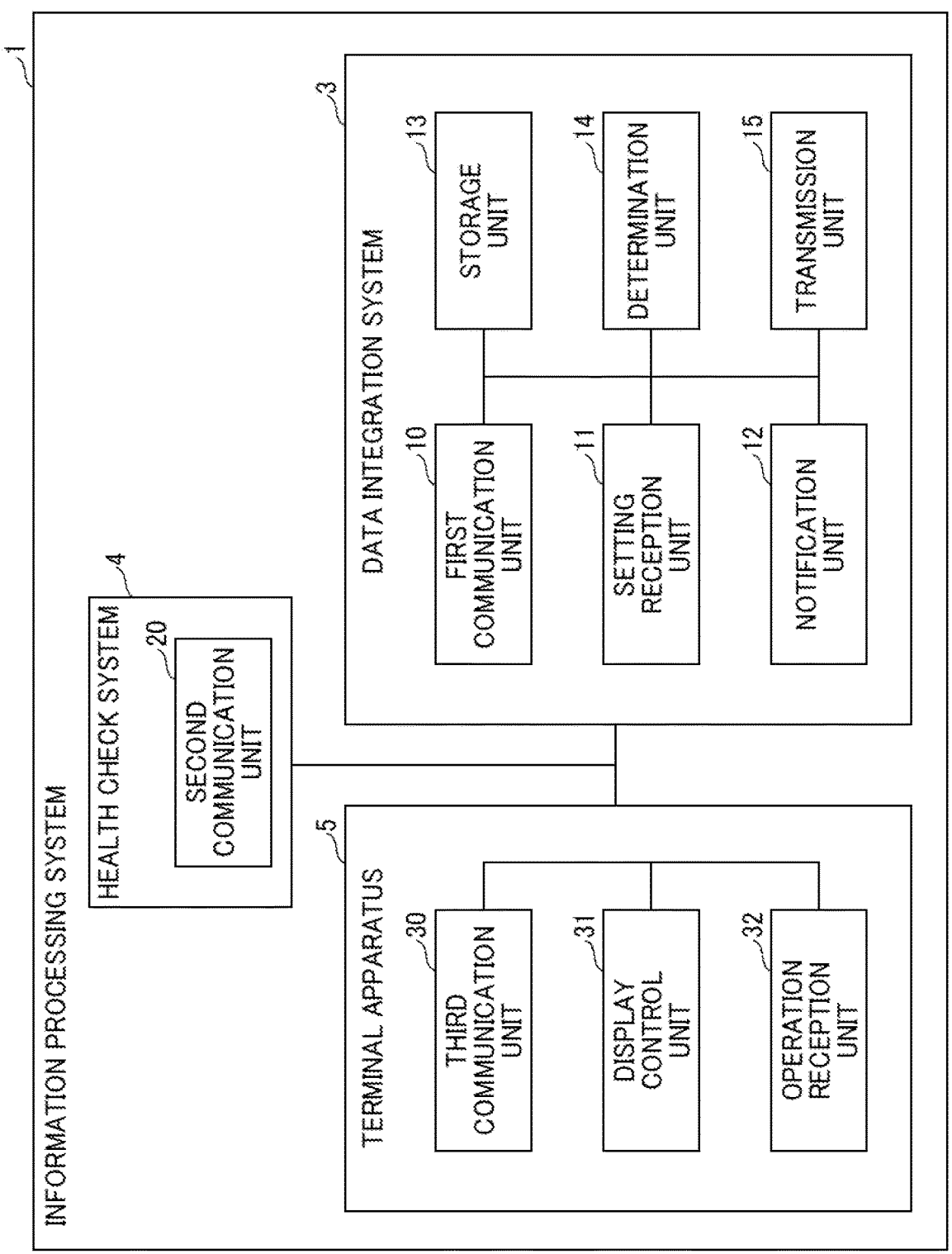
FIG. 3 is a block diagram illustrating an example of a functional configuration of the information processing, system according to the embodiment of the present disclosure.

FIG. 3 is a block diagram illustrating an example of a functional configuration of the information processing system 1 according to the first embodiment of the present disclosure.

The data integration system 3 includes a first communication unit 10, a setting reception unit 11, a notification unit 12, a determination unit 14, and a transmission unit 15. These functional units are functions or units that are implemented by the CPU 501 executing commands included in one or more programs installed on the information processing apparatus that serves as the data integration system 3. Some of the functions or units such as the first communication unit 10, the notification unit 12, and the transmission unit 15 are implemented by the network I/F 509 controlled by the CPU 501, for example. The data integration system 3 further includes a storage unit 13. The storage unit 13 may be implemented by, for example, a storage device having a storage area, such as the HD 504 included in the data integration system 3.

The setting reception unit 11 receives connection destination information such as a uniform resource locator (URL) from a third communication unit 30 of the terminal apparatus of each tenant. The connection destination information is used for identifying a connection destination when the data integration system 3 establishes a connection to the health check system 4 that has acquired the health data, and is referred to as connection destination information of the health check system 4. That is, the connection destination information of the health check system 4 of each tenant is desirably set in the data integration system 3 in advance. The setting reception unit 11 receives a notification rule and setting information related to a transmission destination of a notification from the third communication unit 30 of the terminal apparatus 5 of each tenant. The notification rule is used for determining whether to transmit a notification based on the health data.

The first communication unit 10 is a communication function of the data integration system 3, and transmits and receives information via the communication network 2. For example, the first communication unit 10 accesses the health check system 4, based on the connection destination information, and acquires the health data from the health check system 4. The method of acquiring the health data is not limited to a pull-type method in which the first communication unit 10 of the data integration system 3 accesses the health check system 4 and receives the health data transmitted from the health check system 4 as a response, and may be a push-type method in which the first communication unit 10 receives the health data transmitted from the health check system 4.

If the health data acquired from the health check system 4 of a certain tenant conforms to the notification rule set for the tenant, the notification unit 1 transmits a notification indicating conformity to the notification rule to the transmission destination set in association with the tenant. According to one notification transmission method, for example, the notification unit 12 transmits an email including a message telling details of the notification to an email address of a user set as the transmission destination of the notification. According to another notification transmission method, the notification unit 12 transmits information for displaying the details of the notification to an application installed on the mobile terminal 8 used by the user.

The storage unit 13 stores the connection destination information of the health check system 4, the notification rule, and the setting information related to the transmission destination that have been received by the setting reception unit 11 in the storage area on a tenant-by-tenant basis.

Based on the notification rule stored in the storage unit 13, the determination unit 14 determines whether to transmit a notification based on the health data. In accordance with a result of this determination, the notification unit 12 transmits a notification indicating conformity to the notification rule.

In response to a request transmitted by the terminal apparatus 5 operated by the user, the transmission unit 15 transmits, to the terminal apparatus 5, screen information of a notification transmission destination setting screen to be displayed by the terminal apparatus 5.

The health check system 4 includes a second communication unit 20. The second communication unit 20 is a communication function of the health check system 4, and transmits and receives information via the communication network 2. For example, the second communication unit 20 receives the health data from the third communication unit 30 of the terminal apparatus 5 belonging to the same tenant as the health check system 4. The second communication unit 20 transmits the health data to the first communication unit 10 of the data integration system 3. The health check system 4 may be implemented by the information processing apparatus described in FIG. 2. The second communication unit 20 is implemented by the network I/F 509, for example. The received health data may be stored at least temporarily in a memory of the health check system 4.

The terminal apparatus 5 includes the third communication unit 30, a display control unit 31, and an operation reception unit 32. These functional units are functions or units that are implemented by the CPU 501 executing command included in one or more programs installed on the information processing apparatus that serves as the terminal apparatus 5.

The third communication unit 30 is a communication function of the terminal apparatus 5, and transmits and receives information via the communication network 2. For example, the third communication unit 30 transmits the health data to the second communication unit 20 of the health check system 4 belonging to the same tenant as the terminal apparatus 5. The third communication unit 30 transmits the connection destination information of the health check system 4, the notification rule, and the setting information related to the transmission destination of a notification to the setting reception unit 11 of the data integration system 3.

The display control unit 31 uses the screen information received via the communication network 2 to display a screen such as a login screen or a setting screen on the display 506 of the terminal apparatus 5. The screen information may be, for example, data of a webpage written in hypertext markup language HTML) or the like. If the screen information is data of a webpage, the display control unit 31 displays the webpage via a web browser or the like.

The operation reception unit 32 receives an operation such as inputting of characters or pressing of a button performed by a user or administrator via the keyboard 511 or the pointing device 512 of the terminal apparatus 5.

Pre-Setting Process

Figures 4, 5:
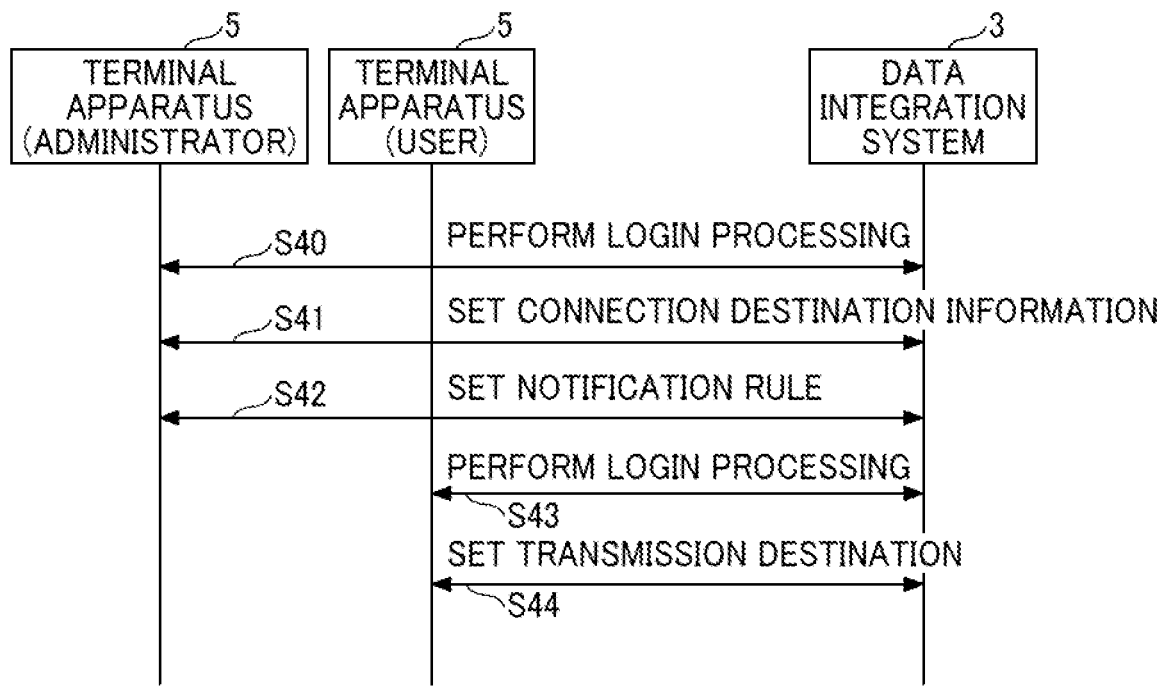
FIG. 4 is a sequence diagram illustrating an example of a pre-setting process according to the embodiment of the present disclosure.
FIG. 5 is a diagram illustrating an example of a user table according to the embodiment of the present disclosure.

FIG. 4 is a sequence diagram illustrating an example of a pre-setting process according to the first embodiment of the present disclosure. This sequence relates to a pre-setting process performed on the data integration system 3 by an administrator and a user who belong to a tenant A. Processing of each step of FIG. 4 will be described below.

Step 40: The administrator of the tenant A operates the terminal apparatus 5 such as the notebook PC 7 to log into the data integration system 3. Specifically, the third communication unit 30 of the terminal apparatus 5 receives screen information of a login screen from the first communication unit 10 of the data integration system 3. The display control unit 31 of the terminal apparatus 5 uses the received screen information to display the login screen on the terminal apparatus 5. The operation reception unit 32 of the terminal apparatus 5 receives an input operation related to authentication information (a tenant ID, a user ID, and a password) used for login of the administrator. The third communication unit 30 transmits the authentication information received by the operation reception unit 32 to the first communication unit 10 of the data integration system 3. The data integration system 3 uses the received authentication information, to perform authentication processing. For example, in the authentication processing, the received authentication information is compared with each record of a user table stored in the storage unit 13 of the data integration system 3.

FIG. 5 is a diagram illustrating an example of the user table according to the first embodiment of the present disclosure. A user table 63 illustrated in FIG. 5 is a database included in the data integration system 3, and includes items such as a tenant ID 64, a user ID 65, a password 66, and an email address 67 for each user permitted to log in.

The tenant ID 64 is an identifier for identifying a tenant. The tenant ID 64 is an example of identification information for identifying an organization.

The user ID 65 is an identifier for identifying a user belonging to the tenant.

The password 66 is authentication information used together with the user ID 65 to authenticate the user when the user logs into the data integration system 3.

The email address 67 is an email address of the user. The email address 67 is used, for example, when the notification unit 12 transmits an email including a message telling details of a notification to the user.

In the authentication processing, if the user table 63 stores the tenant ID 64, the user ID 65, and the password 66 respectively matching the tenant ID, the user ID, and the password included in the received authentication information, it is determined that authentication is successful; otherwise, it is determined that authentication is unsuccessful. If authentication is successful, the process proceeds to step S41 in FIG. 4.

Step S41: The administrator of the tenant A operates the terminal apparatus 5 such as the notebook PC 7 to perform an operation of setting the connection destination information of the health check system 4 from Which the data integration system 3 acquires the health data related to the tenant A.

Specifically, the third communication unit 30 of the terminal apparatus 5 receives screen information of a connection destination setting screen for setting the connection destination information from the first communication unit 10 of the data integration system 3. The display control unit 31 of the terminal apparatus 5 uses the received screen information to display the connection destination setting screen on the terminal apparatus 5.

Figures 6, 7:
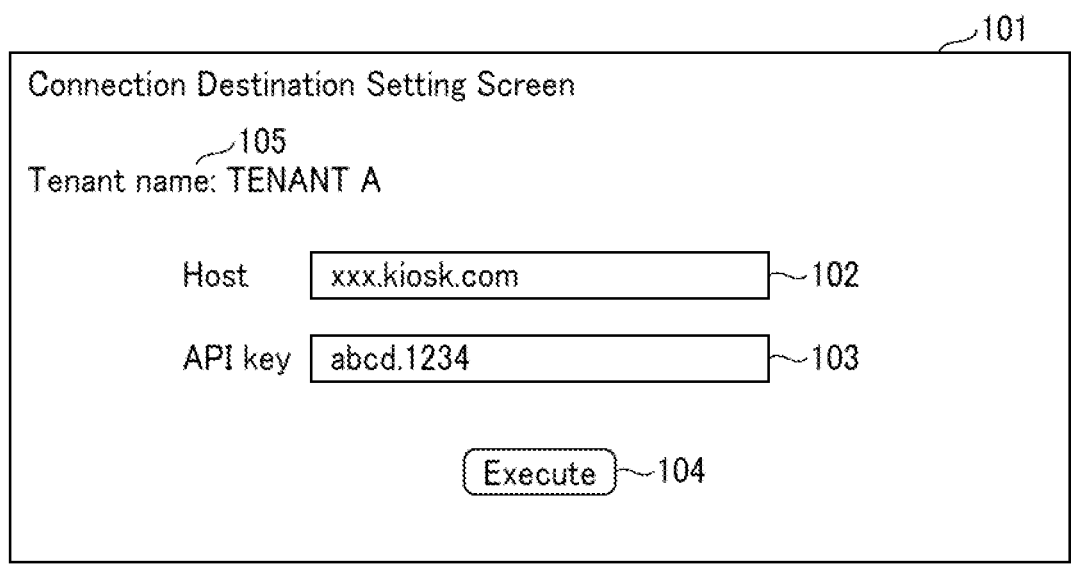
FIG. 6 is a diagram illustrating an example of a connection destination setting screen according to the embodiment of the present disclosure.
FIG. 7 is a diagram illustrating an example of a tenant table according to the embodiment of the present disclosure.

FIG. 6 is a diagram illustrating an example of the connection destination setting screen according to the first embodiment of the present disclosure. A connection destination setting screen 101 illustrated in FIG. 6 includes a host input area 102, an application programming interface (API) key input area 103, an execute button 104, and a tenant name display area 105.

The host input area 102 is an area for receiving an input of a URL of the connection destination (the health check system 4 of the tenant A).

The API key input area 103 is an area for receiving an input of an API key to be used for accessing the connection destination. The API key is information indicating the presence of an access right to the health check system 4. The API key is, for example, a key issued by the health check system 4. The administrator of the tenant A acquires in advance the API key issued by the health check system 4.

The execute button 104 is a button for receiving an instruction (registration instruction) to set the contents (connection destination information) input to the host input area 102 and the API key input area 103.

The tenant name display area 105 displays a tenant name of the tenant for which the connection destination information is set (the tenant to which the successfully logged-in administrator belongs). The tenant is hereinafter referred to as a "target tenant". The tenant name is displayed based on a tenant table stored in the storage unit 13 of the data integration system 3.

FIG. 7 is a diagram illustrating an example of the tenant table according to the first embodiment of the present disclosure. A tenant table 60 illustrated in FIG. 7 is a database included in the data integration system 3, and includes items such as a tenant ID 61 and a tenant name 62.

The tenant ID 61 is an identifier for identifying a tenant. The same value as that of the tenant ID 64 illustrated in FIG. 5 is used for the same tenant.

The tenant name 62 is a name of the tenant identified by the tenant ID 61 and is displayed in the tenant name display area 105 or the like.

If the operation reception unit 32 of the terminal apparatus 5 detects pressing of the execute button 104 after the connection destination information including the URL and the API key is input in the connection destination setting screen 101, the third communication unit 30 transmits the connection destination information to the setting reception unit 11 of the data integration system 3. In response to receiving the connection destination information, the setting reception unit 11 registers the connection destination information in a connection destination information table stored in the storage unit 13 of the data integration system 3.

FIG. 8 is a diagram illustrating an example of the connection destination information table according to the first embodiment of the present disclosure. A connection destination information table 68 illustrated in FIG. 8 is a database stored in the storage unit 13 of the data integration system 3, and includes items such as a system ID 69, a tenant ID 70, and connection destination information 71.

The system ID 69 is an identifier for identifying the health check system 4.

The tenant ID 70 is an identifier for identifying a tenant that uses the health check system 4 identified by the system ID 69. The same value as that of the tenant ID 64 illustrated in FIG. 5 is used for the same tenant.

The connection destination information 71 is connection destination information to be used when the data integration system 3 accesses the health check system 4. In the connection destination information 71, "host" indicates the URL input to the host input area 102 in FIG. 6. Likewise, "apikey" indicates the API key input to the API key input area 103 in FIG. 6.

A new record is added to the connection destination information table 68. The connection destination information received by the setting reception unit 11 is registered in the record in association with the tenant ID of the target tenant. The system ID of the record may be assigned by the setting reception unit 11 when the record is generated, or a value registered in advance in association with the tenant ID may be registered.

Step S42: The administrator of the tenant A operates the terminal apparatus 5 such as the notebook PC 7 to set a notification rule used by the data integration system 3 to determine whether to transmit a notification based on the health data.

Specifically, the third communication unit 30 of the terminal apparatus 5 receives screen information of a notification rule setting screen for setting the notification rule from the first communication unit 10 of the data integration system 3. The display control unit 31 of the terminal apparatus 5 uses the received screen information to display the notification rule setting screen on the terminal apparatus 5.

FIG. 9 is a diagram illustrating an example of the notification rule setting screen according to the first embodiment of the present disclosure. A notification rule setting screen 110 illustrated in FIG. 9 includes a rule ID selection area 111, an add button 112, a delete button 113, a field input area 114, a relational operator input area 115, a threshold value input area 116, and an execute button 117.

The rule ID selection area 111 displays, as a candidate to be selected, a rule ID 82 that has already been registered and is selectable by the administrator. The add button 112 is a button for receiving an instruction to add a new notification rule. For example, in response to pressing of the add button 112, a pop-up screen for inputting a new rule ID is displayed. If a new rule ID is input in the pop-up screen, the rule ID is added to the rule ID selection area 111 and is selected. The delete button 113 is a button for receiving an instruction to delete a notification rule corresponding to the rule ID 82 selected in the rule ID selection area 111. That is, the administrator is permitted to not only create a new notification rule but also change or delete an already set notification rule. The field input area 114 is an area for receiving an input of a field 84 (item) to be compared with a threshold value 86 in a conditional expression indicated by the notification rule. The relational operator input area 115 is an area for receiving an input of a symbol indicating a relationship between the field 84 and the threshold value 86 in the conditional expression indicated by the notification rule. The relational operator input area 115 is an area in which a relational operator 85 is input. The threshold value input area 116 is an area for receiving an input of the threshold value 86 in the conditional expression indicated by the notification rule. The execute button 117 is a button for receiving an instruction to register the contents set in the notification rule setting screen 110.

If the operation reception unit 32 of the terminal apparatus 5 detects pressing of the execute button 117 after (constituent items of) the notification rule is input in the notification rule setting screen 110, the third communication unit 30 transmits a request to register the notification rule to the setting reception unit 11 of the data integration system 3. In response to receiving the registration request, the setting reception unit 11 of the data integration system 3 registers the notification rule included in the registration request in a notification rule table stored in the storage unit 13 of the data integration system 3.

FIG. 10 is a diagram illustrating an example of the notification rule table according to the first embodiment of the present disclosure. A notification rule table 81 illustrated in FIG. 10 is a database stored in the storage unit 13 of the data integration system 3, and includes items such as the rule ID 82, a tenant ID 83, the field 84, the relational operator 85, and the threshold value 86.

The rule ID 82 is an identifier for identifying a notification rule.

The tenant ID 83 is an identifier for identifying a tenant that uses the notification rule. The same value as that of the tenant ID 64 illustrated in FIG. 5 is used for the same tenant.

The field 84 is information indicating a type of the health data. The health data will be described later.

The relational operator 85 is a relational operator used in the notification rule. That is, the notification rule is defined such that a notification is made if a value of the received health data satisfies a condition (conditional expression) indicated by the relational operator 85 and the threshold value 86.

The threshold value 86 is used to define the condition of the notification rule. For example, suppose that the relational operator 85 is ">=" and the threshold value 86 is "99.5". In this case, if the body temperature (temperature) of the received health data is 99.5 degrees Fahrenheit (equivalent to 37.5 degrees Celsius) or higher, the condition of the notification rule is met, so that a notification is transmitted.

If the notification rule received by the setting reception unit 11 is a notification rule including a new rule ID, the setting reception unit 11 generates a new record in the notification rule table 81. The setting reception unit 11 registers the received notification rule and the tenant ID of the target tenant in the record.

Step S43: To set a transmission destination of a notification, the user belonging to the tenant A operates the terminal apparatus 5 such as the notebook PC 7 to log into the data integration system 3. Specific login processing is substantially the same as that performed in step S40.

Step S44: The user belonging to the tenant A operates the terminal apparatus 5 such as the notebook PC 7 to set the transmission destination to which the data integration system 3 transmits a notification based on the health data.

Specifically, the third communication unit 30 of the terminal apparatus 5 receives screen information of a notification transmission destination setting screen for setting the transmission destination of a notification from the first communication unit 10 of the data integration system 3. The display control unit 31 of the terminal apparatus 5 uses the received screen information to display the notification transmission destination setting screen on the terminal apparatus 5.

FIG. 11 is a diagram illustrating an example of the notification transmission destination setting screen according to the first embodiment of the present disclosure. A notification transmission destination setting screen 121 illustrated in FIG. 11 includes a rule ID selection area 122, transmission destination selection areas 123 and 124, delete buttons 125 and 126, an add button 127, and an execute button 128.

The rule ID selection area 122 is an area for receiving selection of a notification rule for which the transmission destination is set. For example, in the rule ID selection area 122, the rule ID 82 of the notification rule set by the administrator in step S42 is displayed as a candidate to be selected.

Each of the transmission destination selection areas 123 and 124 is an area for receiving selection of a user who is the transmission destination of the notification. For example, in each of the transmission destination selection areas 123 and 124, the user ID 65 of the user belonging to the same tenant as the user who is performing the operation in the user table 63 illustrated in FIG. 5 is displayed as a candidate for a user to be selectable as the transmission destination. The delete buttons 125 and 126 are buttons for receiving instructions to delete the transmission destinations selected in the transmission destination selection areas 123 and 124, respectively. The add button 127 is a button for receiving an instruction to add a transmission destination. The execute button 128 is a button for receiving an instruction to register the contents set in the notification transmission destination setting screen 121.

Figure 12:
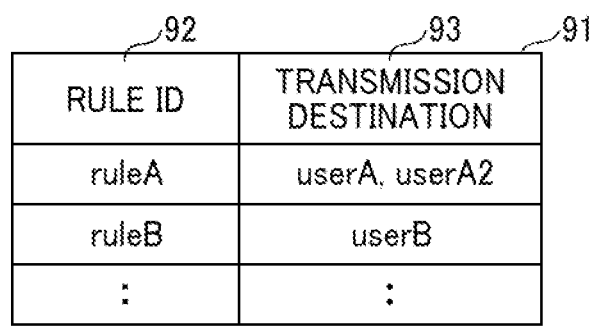
FIG. 12 is a diagram illustrating an example of a notification transmission destination table according to the embodiment of the present disclosure.

If the operation reception unit 32 of the terminal apparatus 5 detects pressing of the execute button 128 after the settings are input in the notification transmission destination setting screen 121, the third communication unit 30 transmits the setting information input to the notification transmission destination setting screen 121 to the setting reception unit 11 of the data integration system 3. In response to receiving the setting information, the setting reception unit 11 registers the setting information in a notification transmission destination table stored in the storage unit 13 of the data integration system 3. FIG. 12 is a diagram illustrating an example of the notification transmission destination table according to the first embodiment of the present disclosure. A notification transmission destination table 91 illustrated in FIG. 12 is a database stored in the storage unit 13 of the data integration system 3, and includes items such as a rule ID 92 and a transmission destination 93.

The rule ID 92 is an identifier for identifying a notification rule, and is set in the rule ID selection area 122 in FIG. 11.

The transmission destination 93 is the user ID 65 of the user who is the transmission destination of a notification and is selected in the transmission destination selection area 123 or 124 in FIG. 11. The user IDs 65 of a plurality of users may be set in the transmission destination 93.

In this example, the setting reception unit 11 generates a new record in the notification transmission destination table 91, and registers the received setting information (the rule ID and the transmission destination) in the record.

Note that the transmission destination of the notification is set in step S44 in accordance with an operation performed by the administrator.

As indicated by the process described above, the information processing system 1 allows the transmission destination of a notification related to health data to be set in accordance with an operation performed by a user. The information processing system 1 allows information on a user belonging to the same tenant as the tenant to which the user who makes the settings belongs to be displayed in the notification transmission destination setting screen 121 as a candidate to be selected as the user who is the set transmission destination of a notification.

Notification Transmission Process

Figure 13:
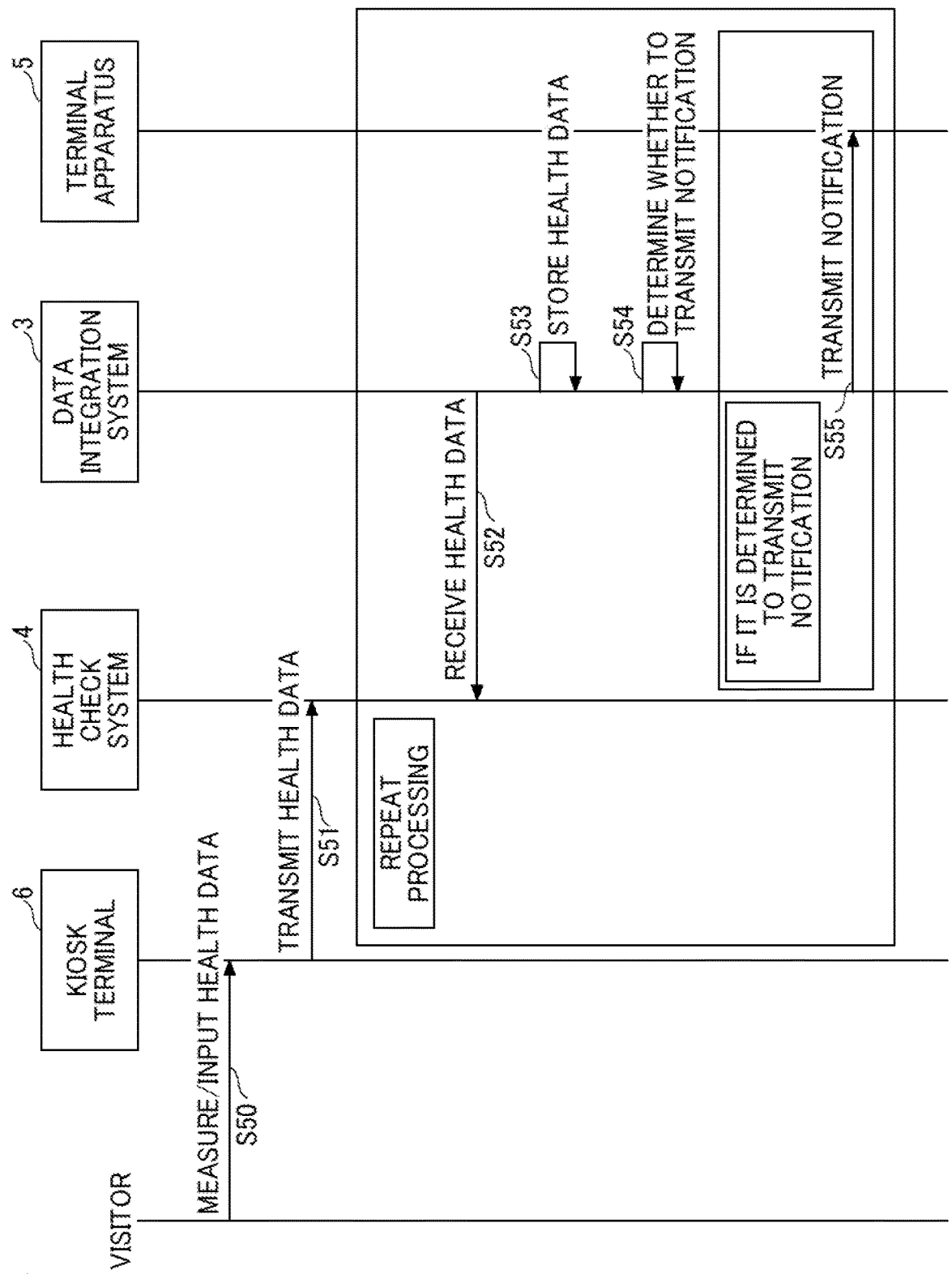
FIG. 13 is a sequence diagram illustrating an example of a notification transmission process according to the embodiment of the present disclosure.

FIG. 13 is a sequence diagram illustrating an example of a notification transmission process according to the first embodiment of the present disclosure. This sequence is related to a process in which the data integration system 3 transmits a notification based on health data acquired from the health check system 4, based on the notification rule and the setting information related to the transmission destination of a notification that are stored through the pre-setting process illustrated in FIG. 4. Processing of each step of FIG. 13 will be described below.

Step S50: A visitor uses the kiosk terminal 6 to measure health data or input information related to the health data when entering a building. In one example, the kiosk terminal 6 measures a body temperature of an entering person (visitor) with the temperature sensor or detects whether the entering person is wearing a mask through image capturing with the camera and image recognition on the captured image. In another example, the kiosk terminal 6 detects a hand of the visitor with the sensor and injects hand sanitizer onto the hand of the visitor. In still another example, the visitor selects the symptom which the visitor has from a list of symptoms displayed on a screen of the kiosk terminal 6 to confirm the subjective symptoms.

Step S51: The kiosk terminal 6 transmits the health data acquired in step S50 to the second communication unit 20 of the health check system 4.

FIG. 14 is a diagram for describing the health data according to the first embodiment of the present disclosure. A health data description table 76 illustrated in FIG. 14 includes items such as a field 77, a data format 78, an explanation 79, and an example value 80.

The field 77 indicates a type of data (item) included in health data 75. The field 77 and data following the field 77 are separated by colon ":".

The data format 78 indicates a format of data to be stored. For example, "INT" indicates an integral value represented in 32 bits or 64 bits. "DateTime" indicates data representing the date and time. "String" indicates data of a character string. "Boolean" indicates data having binary values such as true and false. FIG. 14 indicates that, for the field 77 "mask_detection", there are four kinds of the data format 78 including "MASK OK (correctly wearing a mask")", "MASK NOT OK" (not correctly wearing a mask). "NO MASK" (not wearing a mask), and "Unknown" (no information about wearing of a mask).

The explanation 79 is an explanation for the details of each field 77 of the health data.

The example value 80 is an example of a specific value of each field 77 of the health data.

Step S52: To acquire health data, the first communication unit 10 of the data integration system 3 periodically (for example, at intervals of 10 minutes) accesses the health check system 4 corresponding to the connection destination information set in step S41 in FIG. 4. In response to the access, the first communication unit 10 of the data integration system 3 receives the health data from the second communication unit 20 of the health check system 4.

Step S53: The first communication unit 10 registers the received health data health data table stored in the storage unit 13.

FIG. 15 is a diagram illustrating an example of the health data table according to the first embodiment of the present disclosure. A health data table 72 illustrated in FIG. 15 includes items such as a tenant ID 73, a data generation date 74, and the health data 75.

The tenant ID 73 is an identifier for identifying a tenant corresponding to the health data 75. The same value as that of the tenant ID 61 illustrated in FIG. 7 is used for the same tenant.

The data generation date 74 indicates a registration date of the health data 75 in the health data table 72.

The health data 75 is the health data illustrated in FIG. 14.

Step S54: Based on the notification rule set in step S42 in FIG. 4, the determination unit 14 of the data integration system 3 determines whether to transmit a notification for the health data received in step S53. For example, if the relational operator 85 and the threshold value 86 of the set notification rule are respectively ">=" and "99.5" in the notification rule table 81 in FIG. 10 and if the "temperature" value in the field 84 of the received health data is "99.8" the determination unit 14 determines to transmit a notification.

Step S55: If the determination unit 14 determines to transmit a notification, the notification unit 12 of the data integration system 3 transmits the notification to the transmission destination set in step S44 in FIG. 4. According to one notification transmission method, for example, the notification unit 12 transmits an email including a message telling details of the notification to the email address of the user set as the transmission destination. For example, the notification unit 12 acquires the email address 67 based on the user ID 65 with reference to the user table 63 illustrated in FIG. 5. This enables identification of the email address of the user.

FIG. 16 is a diagram illustrating an example of the email of the notification based on the health data according to the first embodiment of the present disclosure. An email 130 illustrated in FIG. 16 includes a sender ("From") 131, an addressee ("To") 132, a subject 133, and a message body 134. The sender 131 indicates an email address of a sender (transmission source) of the email 130. For example, the email address of the data integration system 3 is set as the sender 131. The addressee 132 indicates an email address of a transmission destination of the email 130 (transmission destination of a notification). The subject 133 indicates a subject of the email 130. The subject may be a character string determined in advance. The message body 134 indicates a message body of the email 130. For example, the health data or the like is inserted to a template set in advance as the message body, so that the message body may be generated.

Another notification transmission method is a (push notification) method for causing the details of the notification to be displayed in a screen of an application installed on the mobile terminal 8 used by the user.

Figure 17A:
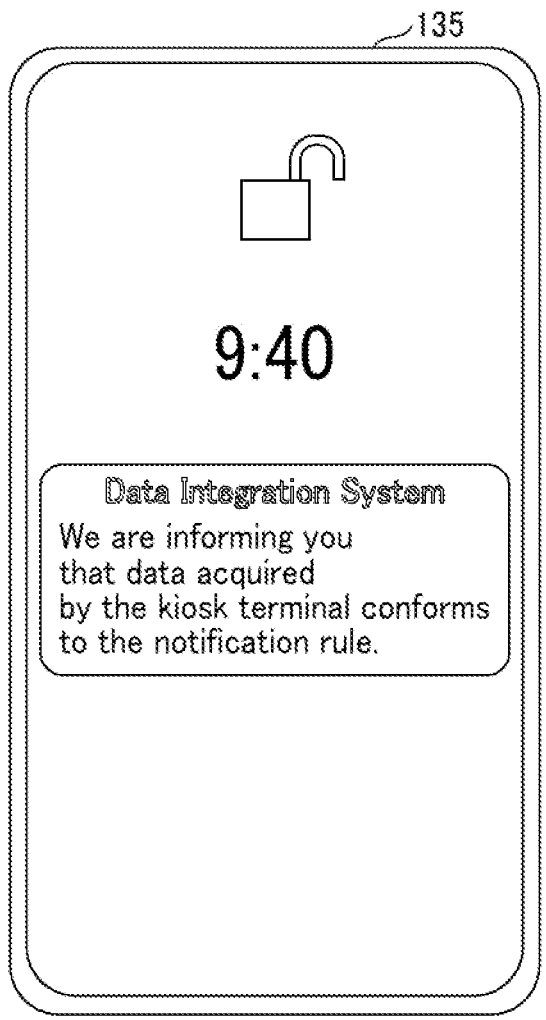
FIGS. 17A and 17B are each a diagram illustrating an example of a notification screen in a mobile application according to the embodiment of the present disclosure.
Figure 17B:
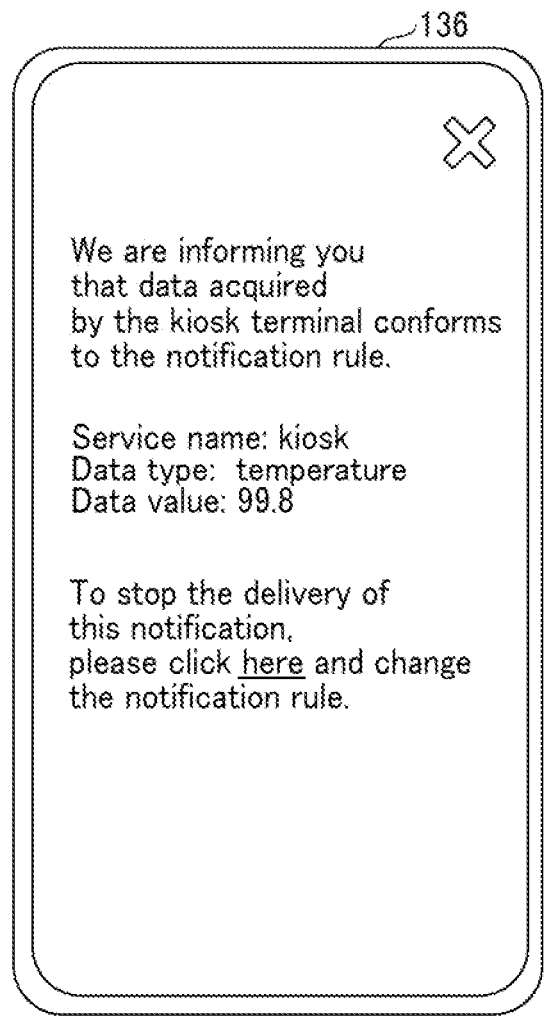

FIGS. 17A and 17B are each a diagram illustrating an example of a notification screen in a mobile application according to the first embodiment of the present disclosure. A notification screen 135 in FIG. 17A, which indicates receipt of a notification, is displayed on a display screen of the mobile terminal S used by the user. A notification screen 136 in FIG. 17B, which presents the details of the notification, is displayed after the user unlocks the mobile terminal 8.

Still another notification transmission method is a method in which the first communication unit 10 of the data integration system 3 transmits screen information of the notification screen to be displayed on the terminal apparatus 5 to the third communication unit 30 of the terminal apparatus 5, in response to a request that is transmitted in response to the user operating the terminal apparatus 5.

Thereafter, processing of steps S52 to S55 is repeatedly performed for each piece of acquired health data. If the determination unit 14 determines not to transmit a notification as a result of the determination in step S54, the process returns to processing in step S52 and the processing is performed on the next piece of health data. If a plurality of pieces of health data are acquired in a certain period and the determination unit 14 determines to transmit a notification for two or more pieces of health data among the plurality of pieces of data, the notification may be collectively transmitted or collectively displayed.

The process described above enables the information processing system 1 to transmit a notification to a predetermined transmission destination set in advance, if the received health data satisfies a predetermined condition of the notification rule set in advance. That is, the information processing system 1 includes a setting reception unit, a communication unit, and a notification unit. The setting reception unit receives, from a user, a setting of a transmission destination of a notification to be transmitted if a notification condition set for information acquired to check a health condition acquired from a person who visits a predetermined place and information that affects health of the person is satisfied. The communication unit receives the acquired information. The notification unit transmits a notification to the transmission destination indicated by the setting in response to the received acquired information satisfying the notification condition.

Second Embodiment

Details of a second embodiment different from those of the first embodiment will be described. In the first embodiment, the data integration system 3 periodically accesses the health check system 4 to acquire health data. The second embodiment is different from the first embodiment in that the health check system 4 periodically accesses the data integration system 3 to transmit health data. That is, in the second embodiment, step S41a described below is performed instead of step S41 of the pre-setting process illustrated in FIG. 4.

Step S41a: The administrator operates the terminal apparatus 5 such as the notebook PC 7 to set, in the health check system 4, connection destination information of the data integration system 3 that is the transmission destination of the health data. Specifically, the third communication unit 30 of the terminal apparatus 5 receives screen information of a setting screen for setting the connection destination information from the health check system 4. The display control unit 31 of the terminal apparatus 5 uses the received screen information to display the setting screen on the terminal apparatus 5. The operation reception unit 32 of the terminal apparatus 5 receives an input operation for setting the connection destination information performed by the administrator. The third communication unit 30 transmits the setting information related to the connection destination received by the operation reception unit 32 to the second communication unit 20 of the health check system 4. The health check system 4 stores the received setting information related to the connection destination therein.

In the second embodiment, the health check system 4 transmits the health data to the data integration system 3 corresponding to the set connection destination information. That is, in the second embodiment, step S52a described below is performed instead of step S52 in FIG. 13.

Step S52a: The second communication unit 20 of the health check system 4 periodically for example, at intervals of 10 minutes) transmits the health data to the first communication unit 10 of the data integration system 3 corresponding to the set connection destination information.

Except for the processing described above, substantially the same processing as that in the first embodiment is performed.

Third Embodiment

Details of a third embodiment different from those of the first or second embodiment will be described. In the third embodiment for example, if different expressions such as "temperature" and "temp" are present, for different health check systems 4, in the field 77 indicating the body temperature in the health data description table 76 illustrated in FIG. 14, the different expressions are treated as the same item in the notification rule. That is, the health check system 4 is a system built by a tenant. Thus, the health check system 4 of a certain tenant and the health check system 4 of another tenant may have a mismatch in an item name of each constituent item of the health data. In the third embodiment, a method of handling such a mismatch will be described.

FIGS. 18A, 18B, and 18C are each a diagram illustrating an example of a notification rule table according to the third embodiment of the present disclosure. A notification rule table 140 illustrated in FIG. 18A is a database stored in the storage unit 13 of the data integration system 3, and includes items such as a rule ID 141, a tenant ID 142, a data type 143, a relational operator 144, and a threshold value 145.

The rule ID 141, the tenant ID 142, the relational operator 144, and the threshold value 145 are the same as the rule ID 82, the tenant ID 83, the relational operator 85, and the threshold value 86 that are the items of the notification rule table 81 illustrated in FIG. 10, respectively.

The data type 143 is used instead of the field 84 of the notification rule table 81 illustrated in FIG. 10. For example, the data type 143 is used for treating different expressions as the same item if the different expressions are in the field 84 for different health check systems 4. That is, the data type 143 is an abstract item of the field 84.

Likewise, a data type table 147 illustrated in FIG. 18B and a system data type table 150 illustrated in FIG. 18C are also databases stored in the storage unit 13 of the data integration system 3. The data type table 147 defines a data name 149 for the data type 143. For example, the data type 143 "dataTypeA" has the data name 149 "temperature" and indicates that data with "dataTypeA" is data related to the body temperature.

The system data type table 150 is a table that defines a correspondence between a field and a data type defined in each health check system 4, and includes, for each correspondence, the data type 143, a system ID 152, and a field 153. The system ID 152 is identification information of the health check system 4. The field 153 is a field corresponding to the data type 143 in the health check system 4 associated with the system ID 152. For example, the health check systems 4 of which the system ID 152 is "systems" and "systemB" respectively use "temperature" and 'temp' as the field 153 of "dataTypeA" that is the data type 143 indicating information related to the body temperature.

When determining whether to transmit a notification based on the health data in the processing of step S54 in FIG. 13, the determination unit 14 of the data integration system 3 refers to the notification rule table 140, the data type table 147, and the system data type table 150. Thus, even if the plurality of health check systems 4 use different expressions in the field 153, those different expressions are handled by using the same data type 143 in the notification rule table 140. That is, among the items included in the health data, items of which expressions are different for different transmission sources are handled as the same item.

While some embodiments of the present disclosure have been described above, such embodiments do not limit the present disclosure in any way. Various modifications and replacements may be made within a scope not departing from the gist of the present disclosure.

Any one of the above-described operations may be performed in various other ways, for example, in an order different from the one described above.

For example, an example of the block diagram of the functional configuration illustrated in FIG. 3 presents blocks obtained by dividing major functions to make it easier to understand the processes performed by the information processing apparatuses included in the information processing system 1 and the data integration system 3. No limitation is intended by how the functions are divided by process or by the name of the functions. The processes performed by the information processing apparatuses may be divided into more processing units in accordance with contents of the processes. Further, the division may be made such that each unit of processing includes more processing.

Each of the functions of the embodiments described above may be implemented by one or more processing circuits or circuitry. The term "processing circuit or circuitry" used herein refers to a processor that is programmed to carry out each function by software such as a processor implemented by an electronic circuit, or a device such as an application specific integrated circuit (ASIC), digital signal processor (DSP), field programmable gate array (FPGA), or existing circuit module that is designed to carry out each function described above.

The apparatuses described in one or more embodiments are just one example of plural computing environments that implement the one or more embodiments disclosed herein. In some embodiments, the information processing system 1 and the information processing apparatus include multiple computing devices, such as a server cluster. The multiple computing devices are configured to communicate with one another through any type of communication link including a network, shared memory, etc., and perform the processes disclosed herein.

The first communication unit 10, the second communication unit 20, and the third communication unit 30 may be simply referred to as communication units, and the order "first", "second", and "third" may be switched if the first communication unit 10, the second communication unit 20, and the third communication unit 30 are clearly distinguishable from one another.

Figure 19:
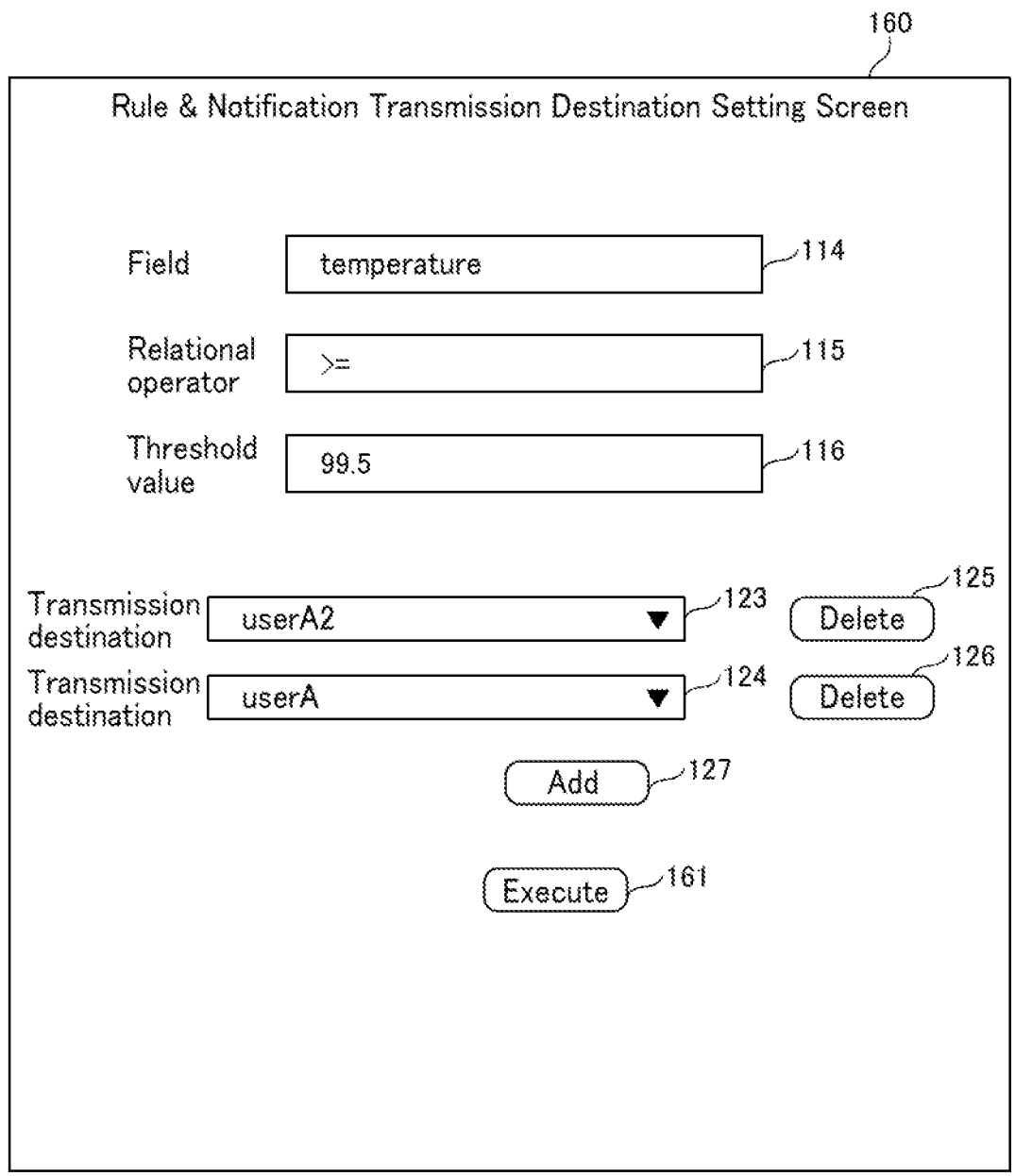
FIG. 19 is a diagram illustrating an example of a screen for setting a rule and a transmission destination of a notification according to still another embodiment of the present disclosure.

In the embodiments above, the example has been described in which the notification rule and the transmission destination of a notification are set in separate screens, i.e., the notification rule setting screen 110 illustrated in FIG. 9 and the notification transmission destination setting screen 121 illustrated in FIG. 11, respectively. However, the notification rule and the transmission destination of a notification may be set in a single screen. FIG. 19 depicts an example of a screen 160 for setting a notification rule and a transmission destination of a notification in a single screen. The operation reception unit 32 of the terminal apparatus 5 receives an input of settings related to a notification rule (the field input area 114, the relational operator input area 115, and the threshold value input area 116) and settings related to a transmission destination of a notification (the transmission destination selection areas 123 and 124) via the screen 160. If the operation reception unit 32 of the terminal apparatus 5 detects pressing of an execute button 161 in the screen 160, the third communication unit 30 transmits the settings related to the notification rule and the settings related to the transmission destination of a notification that are set in the screen 160 to the setting reception unit 11 of the data integration system 3.

In the embodiments above, the kiosk terminal 6 is described as an example of a measurement apparatus. However, instead of the kiosk terminal 6, a terminal such as a PC or tablet may be used to acquire health data of a person entering a building or facility. In this case, the terminal such as a PC or tablet uses a thermometer, a camera, or the like connected to the terminal with a cable or wirelessly to acquire health data of the entering person.

In a first aspect, an information processing system is connected, via a network, to a health check system that manages a measurement apparatus that performs measurement to obtain information related to health of a user. The information processing system includes a setting reception unit that receives a first setting and a second setting that are input to a terminal apparatus connected to the information processing system via the network, from the terminal apparatus via the network. The first setting indicates a transmission destination to which a notification based on the information related to health of the user obtained through measurement by the measurement apparatus is transmitted. The second setting indicates a notification condition on which the notification is transmitted to the transmission destination. The information processing system further includes a communication unit that receives, from the health check system via the network, the information related to health of the user obtained through measurement by the measurement apparatus and transmitted from the measurement apparatus to the health check system. The information processing system further includes a notification unit that transmits the notification based on the received information related to health of the user to the transmission destination indicated by the first setting, in response to the received information related to health of the user satisfying the notification condition indicated by the second setting.

In a second aspect, the notification condition includes a plurality of notification conditions, and the setting reception unit of the information processing system according to the first aspect receives the first setting related to the transmission destination, set for each of the plurality of notification conditions.

In a third aspect, the information processing system according to the first aspect or the second aspect further includes a transmission unit that transmits, in response to a request transmitted by the terminal apparatus, screen information for causing one or more setting screens for receiving an input of the first setting and the second setting to be displayed. The setting reception unit receives the first setting and the second setting input via the one or more setting screens.

In a fourth aspect, in the information processing system according to the third aspect, the one or more setting screens include a first setting screen for receiving an input of the first setting and a second setting screen for receiving an input of the second setting.

In a fifth aspect, in the information processing system according to any of the first to fourth aspects, the information related to health of the user includes at least one of information on a body temperature, information as to whether the user is wearing a mask, or information as to whether the user has used hand sanitizer.

In a sixth aspect, the information processing system according to any of the first to fifth aspects further includes a storage unit that stores the first setting and the second setting in a storage area.

In a seventh aspect, in the information processing system according to the sixth aspect, the storage unit stores the first setting and the second setting in the storage area in association with identification information for identifying an organization. The notification unit transmits the notification based on the received information related to health of the user to the transmission destination based on the first setting, response to a not condition based on the second setting stored in association with the organization to which the user related to the received information related to health belongs being satisfied.

In an eighth aspect, in the information processing system according to any of the first to seventh aspects, the communication unit accesses the health check system, based on connection destination information for accessing the health check system, and receives the information related to health of the user transmitted from the health check system in response to the access.

In a ninth aspect, in the information processing system according to the eighth aspect, the connection destination information includes an API key issued by the health check system.

In a tenth aspect, an information processing apparatus communicably connected with a health check system that manages a measurement apparatus and a terminal apparatus. The information processing apparatus includes circuitry configured to: receive a first setting and a second setting that are input to the terminal apparatus, from the terminal apparatus via a network, the first setting indicating a transmission destination of a notification based on information related to health of a user obtained through measurement by the measurement apparatus, the second setting indicating a notification condition on which the notification is transmitted to the transmission destination; receive, from the health check system via the network, the information related to health of the user obtained through measurement by the measurement apparatus and transmitted from the measurement apparatus to the health check system; and transmit the notification based on the received information related to health of the user to the transmission destination indicated by the first setting, in response to the received information related to health of the user satisfying the notification condition indicated by the second setting.

The invention claimed is:

1. An information processing system communicably connected via a network to a health check system that manages a measurement apparatus and a terminal apparatus, the information processing system comprising a memory and circuitry configured to:
   receive a first setting and a second setting that are input to the terminal apparatus, from the terminal apparatus via the network, the first setting indicating a transmission destination of a notification based on information related to health of a user obtained through measurement by the measurement apparatus, the second setting indicating a notification condition on which the notification is transmitted to the transmission destination;
   store in the memory the first setting and the second setting in association with identification information for identifying an organization;
   access the health check system at a specified time;
   in response to the access, receive, from the health check system via the network, the information related to health of the user obtained through measurement by the measurement apparatus and transmitted from the measurement apparatus to the health check system; and
   transmit the notification based on the received information related to health of the user to the transmission destination indicated by the first setting, in response to the received information related to health of the user satisfying the notification condition based on the second setting stored in association with an organization to which the user belongs.

2. The information processing system according to claim 1, wherein the notification condition includes a plurality of notification conditions, and the first setting indicating the notification destination is set for each of the plurality of notification conditions.

3. The information processing system according to claim 1, wherein the circuitry is further configured to:
   transmit screen information to the terminal apparatus in response to a request transmitted from the terminal apparatus, the screen information for causing the terminal apparatus to display one or more setting screens for receiving an input of the first setting and the second setting, and
   receive the first setting and the second setting that are input via the one or more setting screens.

4. The information processing system according to claim 3, wherein the one or more setting screens include a first setting screen for receiving an input of the first setting, and a second setting screen for receiving an input of the second setting.

5. The information processing system according to claim 1, wherein the information related to health of the user includes at least one of information on a body temperature of the user, information indicating whether the user is wearing a mask, or information indicating whether the user has used hand sanitizer.

6. The information processing system according to claim 1, wherein the circuitry is configured to access the health check system, based on connection destination information for accessing the health check system and receive the information related to health of the user transmitted from the health check system in response to the access.

7. The information processing system according to claim 6, wherein the connection destination information includes an API key issued by the health check system.

8. An information processing method comprising:
   receiving a first setting and a second setting that are input to a terminal apparatus, from the terminal apparatus via a network, the first setting indicating a transmission destination of a notification based on information related to health of a user obtained through measurement by a measurement apparatus managed by a health check system, the second setting indicating a notification condition on which the notification is transmitted to the transmission destination;
   storing the first setting and the second setting in association with identification information for identifying an organization;
   accessing the health check system at a specified time;
   in response to the access, receiving, from the health check system via the network, the information related to health of the user obtained through measurement by the measurement apparatus and transmitted from the measurement apparatus to the health check system; and
   transmitting the notification based on the received information related to health of the user to the transmission destination indicated by the first setting, in response to the received information related to health of the user satisfying the notification condition based on the second setting stored in association with an organization to which the user belongs.

9. A non-transitory recording medium storing a plurality of instructions which, when executed by one or more processors, cause the processors to perform an information processing method comprising:
   receiving a first setting and a second setting that are input to a terminal apparatus, from the terminal apparatus via a network, the first setting indicating a transmission destination of a notification based on information related to health of a user obtained through measurement by a measurement apparatus managed by a health check system, the second setting indicating a notification condition on which the notification is transmitted to the transmission destination;

storing the first setting and the second setting in association with identification information for identifying an organization;

accessing the health check system at a specified time;

in response to the access, receiving, from the health check system via the network, the information related to health of the user obtained through measurement by the measurement apparatus and transmitted from the measurement apparatus to the health check system; and transmitting the notification based on the received information related to health of the user to the transmission destination indicated by the first setting, in response to the received information related to health of the user satisfying the notification condition based on the second setting stored in association with an organization to which the user belongs.

\* \* \* \* \*